US005749873A

United States Patent [19]
Fairley

[11] Patent Number: 5,749,873
[45] Date of Patent: May 12, 1998

[54] APPARATUS FOR THE MOBILE FIXATION OF BONES

[76] Inventor: Jeffrey D. Fairley, Haeberlstrasse 5, 80337, Munich, Germany

[21] Appl. No.: 683,620

[22] Filed: Jul. 17, 1996

Related U.S. Application Data

[63] Continuation of Ser. No. 344,938, Nov. 23, 1994, abandoned.

[30] Foreign Application Priority Data

Nov. 26, 1993 [DE] Germany .................. 43 40 398.0

[51] Int. Cl.$^6$ .................................................. A61B 17/80
[52] U.S. Cl. .................................................. 606/70
[58] Field of Search .......................... 606/71, 70, 105, 606/72, 69; 433/173

[56] References Cited

U.S. PATENT DOCUMENTS

| | | | |
|---|---|---|---|
| 2,406,832 | 9/1946 | Hardinge | 606/71 |
| 2,486,303 | 10/1949 | LongFellow | 606/71 |
| 3,547,114 | 12/1970 | Haboush | 606/105 X |
| 4,085,744 | 4/1978 | Lewis et al. | 606/61 |
| 4,096,857 | 6/1978 | Cramer et al. | 606/71 X |
| 4,611,582 | 9/1986 | Duff | 606/61 |
| 5,092,889 | 3/1992 | Campbell | 623/16 |
| 5,129,903 | 7/1992 | Luhr et al. | 606/71 |
| 5,375,823 | 12/1994 | Navas | 623/17 X |
| 5,405,391 | 4/1995 | Henderson et al. | 623/17 |
| 5,466,261 | 11/1995 | Richelsoph | 623/16 |

FOREIGN PATENT DOCUMENTS

| | | | |
|---|---|---|---|
| 0346269 | 12/1989 | European Pat. Off. | 623/17 |
| 1051847 | 1/1954 | France | 606/71 |
| 0867422 | 2/1953 | Germany | 606/71 |
| 2621175 | 11/1977 | Germany | 606/71 |
| 0156570 | 9/1982 | Germany | 606/71 |
| 3722595 | 1/1989 | Germany | 606/105 |
| 3819840 | 12/1989 | Germany | 606/60 |
| 0335797 | 3/1959 | U.S.S.R. | 606/71 |
| 0491382 | 2/1975 | U.S.S.R. | 606/70 |
| 0829103 | 5/1981 | U.S.S.R. | 606/71 |
| 0915840 | 3/1982 | U.S.S.R. | 606/71 |
| 1082420 | 3/1984 | U.S.S.R. | 606/70 |
| 1648419 | 5/1991 | U.S.S.R. | 606/70 |
| 1683723 | 10/1991 | U.S.S.R. | 606/69 |
| 1754085 | 8/1992 | U.S.S.R. | 606/70 |

*Primary Examiner*—David H. Willse
*Attorney, Agent, or Firm*—Michael A. Glenn

[57] ABSTRACT

An apparatus for the mobile fixation of bones in one plane, which has a first assembly plate that can be fixed on the bone by a suitable first fastener and which has a first connecting part and a second assembly plate which can be fixed on the bone by a suitable second fastener, and which has a second connecting part. Optionally, the apparatus has at least one further assembly plate, which can be fixed on the bone by a suitable fastener and it has a further connecting part which is mounted on a connecting element. The connecting element is mounted on the connecting parts so that the movement of the assembly plates is possible in relation to each other in substantially only one plane, and a change of spacing of the assembly plates relative to each other is possible by a predetermined length. All the components of the apparatus must consist of physiologically compatible materials (such as, for example, precious metals, ceramics, plastics, gold-vitallium alloys, titanium, vanadium, high quality steels and alloys thereof, etc.) to prevent a defensive reaction of the human or animal body. At the same time, the materials must be osseointegratable, to allow the bone to grow undisturbed.

7 Claims, 1 Drawing Sheet

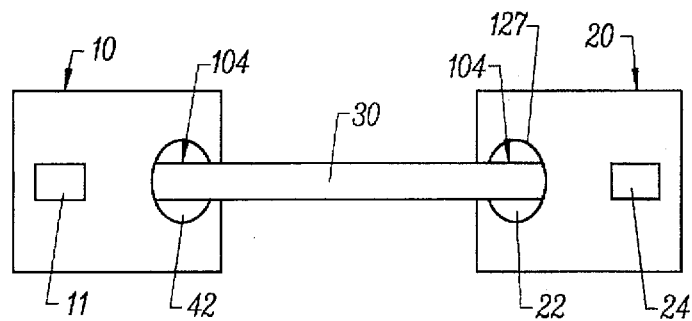
FIG. 1
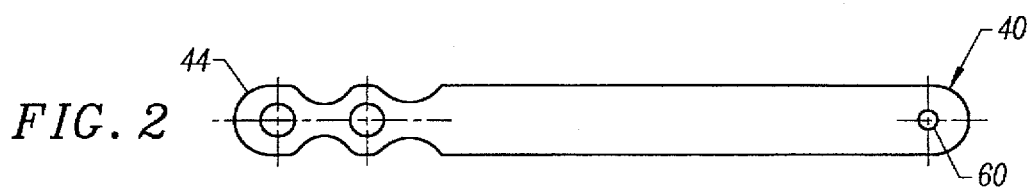
FIG. 2
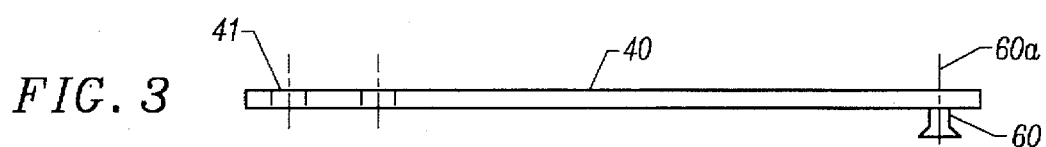
FIG. 3
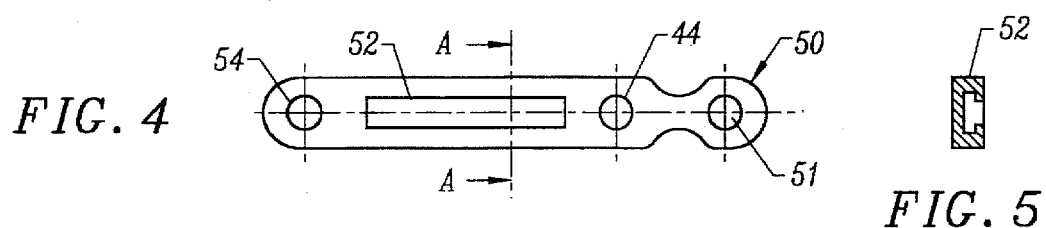
FIG. 4
FIG. 5
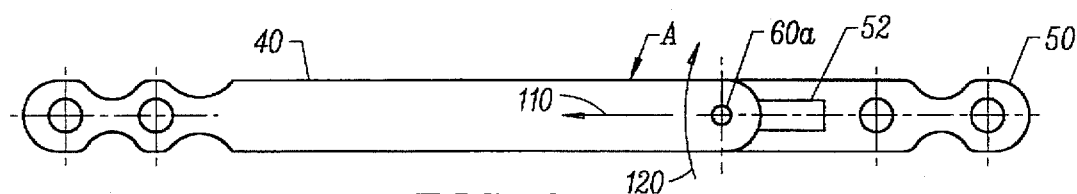
FIG. 6
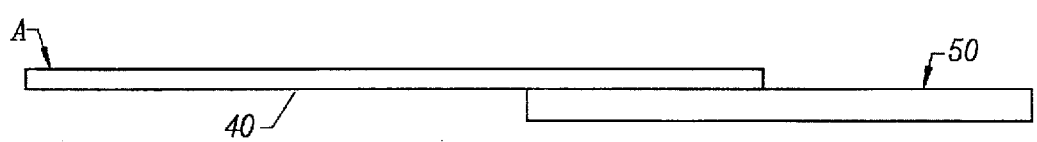
FIG. 7

APPARATUS FOR THE MOBILE FIXATION OF BONES

This is a continuation of application Ser. No. 08/344,938 filed Nov. 23, 1994, now abandoned.

SPECIFICATION

The invention concerns an apparatus for the mobile fixation of bones, in particular in the region of the face and skull or at the extremities of human or animal bodies, in order not to impede dynamic bone growth or desired movements of the bones after surgical operations, such as, for example, operations to correct retrusions of the midface region.

Conventional apparatus for the fixation of bones can be classified as either rigid fixations or variable fixations.

The invention is suitable, in particular, for craniofacial growth, such as in the case of small children who suffer from morbus apart or morbus crouzon or other cranial suture synostoses.

In the case of rigid fixations, plates are firmly connected to the bones by securing elements and thus they fix the position of the bones. The fixing plates are applied below the tissue directly on the bones, and, to the extent that this is necessary, are again removed after performing their function. However, there is the disadvantage in this case that the fixing plates prevent the drifting apart of the bones during growth. In particular for the correction of midfacial retrusion and cranial suture synostoses, however, room for manoeuvre is absolutely necessary, to allow the growth of the bone.

In the case of variable fixations, pins which project through the skin are secured on the bone. Because of an adjustable connecting rod which is arranged on the outside of the body between the pins, the spacing of the pins can be varied so that adaptation of the fixation to the growth process at the moment becomes possible. However, it is a disadvantage that due to the pins which project from the skin, there is a very high risk of infection. In particular, infections which occur on the human scalp after surgical operations may lead to situations which endanger life. In addition, when using such fixing apparatus, a very high degree of psychological stress is observed in the patients and their relatives.

It is the object of the present invention to fix the bones on the point of suture and, on the other hand, to allow the growth of the bones in a direction which is predetermined by the apparatus.

In accordance with the invention, the problem is solved by an apparatus for the mobile fixation of bones which has:

- a first assembly plate, which can be fixed by suitable first fixing means on the bone and which has a first connecting part;
- a second assembly plate, which can be fixed on the bone by suitable second fixing means and which has a second connecting part; and
- optionally at least one further assembly plate, which can be fixed on the bone by suitable fixing means and which has a further connecting part which is mounted on a connecting element; and
- the connecting element, which is mounted on the connecting parts so that the movement of the assembly plates to each other is substantially only possible in one plane and a change in the spacing of the assembly plates from one another is possible by a predetermined length.

Consequently, the apparatus for the mobile fixation of bones comprises two interconnected assembly plates, which are secured by suitable fixing means on the respective bone. The assembly plates are connected with each other by two connecting elements so that movement in one plane is possible without problems.

It is an advantage that the apparatus which is mounted directly on the bone by a surgical operation does not have any components which project outside the skin. Therefore, the risk of infection is clearly reduced. In addition, it is advantageous that because of the displaceability of the assembly plates in relation to each other, the drifting apart of the bone becomes possible, yet the bones can be simultaneously fixed and can remain stable.

All the components of the apparatus must consist of physiologically compatible materials (such as, for example, precious metals, ceramics, plastics, gold-vitallium alloys, titanium, vanadium, high quality steels, alloys thereof etc.), in order to prevent a defensive reaction of the human or animal body. At the same time, the materials must be osseointegratable, so that the bone can grow undisturbed.

In one embodiment, the two assembly plates are firmly connected with each other via a guide pin which is inserted displaceably in a guide slot. Thereby a movement in the longitudinal direction and a rotational movement around the axis of the guide pin are possible. The assembly plates are installed so that the first assembly plate is secured on one bone and the second assembly plate is inserted on the second bone by devices using suitable means, such as screws.

Furthermore, there is the possibility to move deliberately the assembly plates by the use of suitable tensioning devices having the connecting element (such as pressure springs, magnets etc.) so that the apparatus can not only be used to fix the bone fractures, but also for the distraction of bones.

Further objects, features and advantages of the invention will be described in more detail with reference to the drawings, by the following description of an embodiment of the apparatus.

FIG. 1 shows a schematic drawing of the apparatus;

FIG. 2 shows a plan view of the first assembly plate of an embodiment of the apparatus;

FIG. 3 shows a side view of the first assembly plate of an embodiment of the apparatus;

FIG. 4 shows a plan view of the second assembly plate of an embodiment of the apparatus;

FIG. 5 shows a sectional view along the section line A—A of the second assembly plate of an embodiment of the apparatus;

FIG. 6 shows a plan view of the embodiment of the apparatus which is composed of the first and second assembly plates; and FIG. 7 shows a side view of the assembled embodiment of the apparatus which is shown in FIG. 5.

FIG. 1 shows a first and a second assembly plate (10, 20), which are secured detachably on the bones by suitable first and second fixing means (11, 21), such as screws, for example. A connecting element (30) which is secured on a first and second connecting part (12, 22) makes it possible for the first and second assembly plates (10, 20) to move through a predetermined length in one plane.

FIGS. 2 and 3 show an embodiment of the apparatus. Here a first assembly plate (40), which has at least two first devices (41), is secured detachably in the manner known per se on the bone by suitable means, such as screws. In addition, at least one guide pin (60) is arranged at a predetermined spacing from at least two first devices (41). The guide pin (60) is used as the connecting element to the second assembly plate (50).

FIG. 4 shows a second assembly plate (50), which has at least two second devices (51), by means of which the second assembly plate (50) is firmly connected with the bone by suitable means, such as screws. Between two of the second devices (51), an aperture (52) is arranged, which comprises a longitudinally extending guide slot, which has in section a substantially T-shaped profile (see FIG. 4).

FIGS. 6 and 7 show the apparatus which is composed of the first and second assembly plate (40, 50). Here at least one guide pin (60) interacts with the guide slot 52 of the second assembly plate (50) in such a manner that displacement in the longitudinal direction 110 can be performed in one plane by a predetermined amount. Given certain requirements on the apparatus, rotation of the first assembly plate (40) against the second assembly plate (50) may also be desirable in the displacement plane. In the embodiment which is shown, the first assembly plate (40) has only one guide pin (60), which is inserted to be displaceable in the T-shaped guide slot of the second assembly plate (50). By using only one guide pin (60), rotation 120 of the assembly plates (40, 50) in relation to each other is possible in the displacement plane around an axis (60a) of the guide pin (60).

A further possible embodiment is a connecting element (30), which has a telescopic rod. The telescopic rod is attached via the first and second connecting parts (12, 22) on the assembly plates (10, 20) which are secured detachably on the bones by fixing means, such as screws. This telescopic rod permits substantially linear movements of the first and second assembly plates (10, 20). By faking use of at least one rotatable joint in the first or second connecting parts (12, 22) rotational movements within the movement plane are also possible.

To prevent defensive reactions of the human or animal body, all the components of the apparatus must consist of physiologically compatible materials (such as, for example, precious metals, ceramics, plastics, gold-vitallium alloys, titanium, vanadium, high quality steels or alloys thereof etc.). At the same time, the materials must be osseointegratable, so that the bone can grow undisturbed.

In the case of a surgical operation for example, as illustrated by FIG. 1, the assembled apparatus is disposed at the sectioned point of the bone so that the first assembly plate 10 is secured on the first bone and the second assembly plate 20 is secured on the second bone by suitable means, such as screws, wherein the assembly plates 10, 20 are moved together as far as possible. Because of the tension developed within the connecting element (30), the assembly plates 10, 20 can be biased and therefore forces which oppose the bone can be adjusted or the assembly plates can be adjusted to lengthen the bone.

The invention was described to clarify it. Of course, the terminology which was used only serves for the specification and should by no means act restrictively.

Modifications and differences within the framework of the specification are possible, therefore the invention can be carried out in accordance with the protective scope which is specified by the claims, without corresponding to the wording of the specific description.

I claim:

1. A physiologically-compatible apparatus configured to passively but rigidly maintain at least a first bone or bone segment and a second bone or bone segment in a substantially coplanar relation, one to the other, while permitting substantially linear movement of said bones or bone segments along a bone growth axis, said apparatus comprising:

a first assembly plate which is configured to be fixed on said first bone or bone segment by a first fixing means and which has a first connecting part;

a second assembly plate which is configured to be fixed on said second bone or bone segment by a second fixing means and which has a second connecting part;

a connecting element located between said first and second assembly plates, said connecting element being mounted on said first and second connecting parts, said connecting element having a connecting element axis fixedly attached to said second connecting part of said second assembly plate said connecting element having one guide pin having a guide pin axis, said guide pin fixedly attached to said first connecting part of said first assembly plate, said guide pin slidably and rotatably attached to said connecting element axis, so that said first and second assembly plates are configured to be initially moved together as far as possible along said connecting element axis when said first and said second fixing means are fixed on said first and second bones or bone segments, wherein movement of said first and second assembly plates in relation to each other is substantially possible linearly between said guide pin attached to said first connecting part of said first assembly plate along said connecting element axis attached to said second connecting part of said second assembly plate, and rotationally around said guide pin axis of said guide pin, wherein said first and second assembly plates are configured to move freely from each other substantially along said connecting element axis in response to bone growth along said bone growth axis, and wherein said first and second assembly plates and said connecting element are configured to maintain said substantially coplanar relation between said first and second bones or bone segments.

2. An apparatus for the mobile fixation of bones in accordance with claim 1, wherein:

said first fixing means has at least two devices which can be fixed on said first bone or bone segment;

said second fixing means has at least two second devices which can be fixed on said first bone or bone segment;

said first connecting part has means for mounting said connecting element on said first assembly plate; and said second connecting part has means for mounting said connecting element on said second assembly plate.

3. An apparatus for the mobile fixation of bones in accordance with claim 1, wherein said means for fixing said first and second assembly plates on said bones have screws.

4. An apparatus for the mobile fixation of bones in accordance with claim 1, wherein said second connecting part has an aperture formed along said connecting element axis, therein to which one end of said guide pin is displaceably mounted.

5. An apparatus for the mobile fixation of bones in accordance with claim 1, wherein:

said second connecting part comprises a guide slot said connecting element axis, in which a cross-section of said guide is substantially T-shaped; and wherein said guide pin is slidably and rotatably displaced within said T-shaped guide slot.

6. An apparatus for the mobile fixation of bones in accordance with claim 1, wherein the material for the apparatus is composed of osseo-integratable materials.

7. An apparatus for the mobile fixation of bones in accordance with claim 6, wherein the materials for the apparatus are selected from a group which comprises physiologically compatible materials, precious metals, ceramics, plastics, gold-vitallium alloys, titanium, vanadium, high quality steels as well as alloys thereof.

* * * * *